(12) United States Patent
Williams

(10) Patent No.: US 10,898,236 B2
(45) Date of Patent: Jan. 26, 2021

(54) SPINAL ROD IMPLANT EXTENSION

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 43 days.

(21) Appl. No.: 16/240,841

(22) Filed: Jan. 7, 2019

(65) Prior Publication Data

US 2019/0133644 A1 May 9, 2019

Related U.S. Application Data

(62) Division of application No. 15/250,394, filed on Aug. 29, 2016, now Pat. No. 10,194,953.

(60) Provisional application No. 62/241,987, filed on Oct. 15, 2015.

(51) Int. Cl.
| | | |
|---|---|---|
| *A61B 17/70* | (2006.01) | |
| *A61B 17/68* | (2006.01) | |
| *A61B 17/56* | (2006.01) | |

(52) U.S. Cl.
CPC ........ *A61B 17/705* (2013.01); *A61B 17/7005* (2013.01); *A61B 2017/567* (2013.01); *A61B 2017/681* (2013.01)

(58) Field of Classification Search
CPC .... A61B 17/705; A61B 17/7034; A61B 17/56
See application file for complete search history.

(56) References Cited

U.S. PATENT DOCUMENTS

| | | | | |
|---|---|---|---|---|
| 4,742,822 | A * | 5/1988 | Guerriero | A61F 5/3776 5/628 |
| 8,882,803 | B2 * | 11/2014 | Iott | A61B 17/705 606/246 |
| 9,675,382 | B2 * | 6/2017 | Bordeaux | A61B 17/62 |
| 2003/0045874 | A1 * | 3/2003 | Thomas, Jr. | A61B 17/7049 606/250 |
| 2005/0038432 | A1 * | 2/2005 | Shaolian | A61B 17/1671 606/86 A |
| 2007/0043365 | A1 * | 2/2007 | Ritland | A61B 17/705 606/257 |
| 2009/0177232 | A1 * | 7/2009 | Kiester | A61B 17/705 606/260 |
| 2010/0114167 | A1 * | 5/2010 | Wilcox | A61B 17/705 606/250 |
| 2010/0137913 | A1 * | 6/2010 | Khatchadourian | A61B 17/7083 606/258 |
| 2010/0160981 | A1 * | 6/2010 | Butler | A61B 17/705 606/308 |
| 2011/0270314 | A1 * | 11/2011 | Mueller | A61B 17/704 606/264 |
| 2016/0106469 | A1 * | 4/2016 | Iott | A61B 17/705 606/278 |

* cited by examiner

*Primary Examiner* — Ellen C Hammond
(74) *Attorney, Agent, or Firm* — Bell & Manning, LLC

(57) ABSTRACT

A method of mounting a spinal rod extension includes accessing at least a portion of an existing spinal rod. The method also includes removing a locking cap from an existing pedicle screw that secures the existing spinal rod. The method also includes placing a connector portion of the spinal rod extension through a screw head of the existing pedicle screw. The method further includes using a connector to secure the connector portion to the existing spinal rod.

7 Claims, 19 Drawing Sheets

SPINAL ROD IMPLANT EXTENSION

CROSS-REFERENCE TO RELATED APPLICATIONS

The present application is a divisional application of U.S. patent application Ser. No. 15/250,394 filed on Aug. 29, 2016, which claims the priority benefit of U.S. Provisional App. No. 62/241,987 filed on Oct. 15, 2015, the entire disclosures of which are incorporated herein by reference.

BACKGROUND

A spinal rod is a metal cylinder implant used in spinal surgery to stabilize a vertebral segment. In a spinal fusion surgery, a spinal rod can be used to connect screws inserted into adjacent vertebral bodies in order to prevent motion and allow fusion to occur across adjacent spine segments. Rods are used extensively in spine fusion systems.

SUMMARY

A spinal rod extension includes a rod portion, a connector portion, a lip, and a connector. The connector portion is mounted to the rod portion. The connector portion is configured for insertion through a screw head of an existing pedicle screw that is used to secure an existing spinal rod. The lip is mounted to the rod portion, and is configured to engage at least a portion of an end of the existing spinal rod. The connector is configured to secure the connector portion to the existing spinal rod.

A method of mounting a spinal rod extension includes accessing at least a portion of an existing spinal rod. The method also includes removing a locking cap from an existing pedicle screw that secures the existing spinal rod. The method also includes placing a connector portion of the spinal rod extension through a screw head of the existing pedicle screw. The method further includes using a connector to secure the connector portion to the existing spinal rod.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

DETAILED DESCRIPTION

Spinal instrumentation is used to stabilize the spine for spinal fusion operations. Such spinal instrumentation can include a spinal rod which is secured to one or more vertebrae via pedicle screws. Adjacent segment deterioration can occur above or below an instrumented spinal fusion, necessitating more surgery and an overall longer spinal rod. Removing an existing spinal rod and replacing it with another, longer spinal rod is a highly invasive procedure. However, it can be difficult to link in to existing pedicle screw and spinal rod instrumentation, especially when the subsequent surgery is done in a minimally invasive manner through small incisions. Existing devices attempt to allow for minimally invasive spinal rod extensions, but all of the existing mechanisms are designed to bypass the existing pedicle screw heads at the top or bottom of a construct. This makes the connecting device bulky, which can lead to potential complications and/or patient discomfort.

Figure 1:
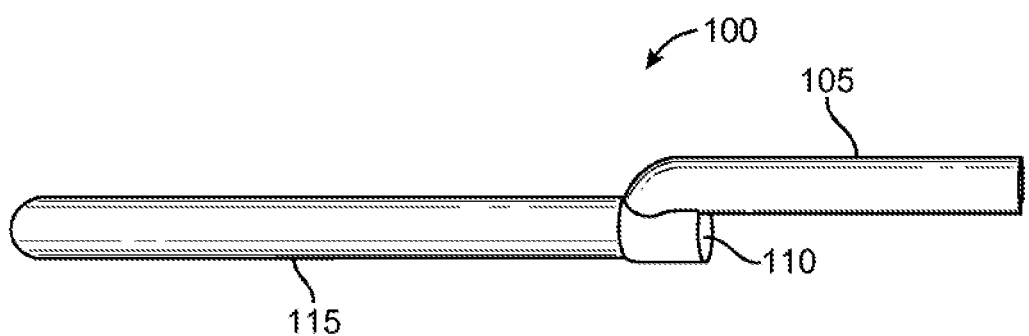
FIG. 1 is a side view of a spinal rod extension in accordance with an illustrative embodiment.

Described herein are spinal rod extensions that allow for minimally invasive surgery, while providing a low profile design that minimizes the bulk of the extension. Specifically, the spinal rod extensions described herein go through existing pedicle screw heads instead of bypassing them. FIG. 1 is a side view of a spinal rod extension 100 in accordance with an illustrative embodiment. The spinal rod extension is a single piece but has three main features or sections. Sections 105 and 110 are designed to attach to an existing spinal rod (not shown), and section 115 (also referred to herein as a rod portion) is the extended length of rod that will attach to new pedicle screws (not shown). Section 105 (also referred to herein as a connector portion) has a curved undersurface (not shown) that fits onto the top of an existing spinal rod (not shown), and section 110 comprises a lip or an opening that accommodates the end of an existing spinal rod, thus enabling mating of the spinal rod extension to an existing spinal rod. In an alternative embodiment, spinal rod extension 100 can be comprised of two or more pieces, with a hinge or other articulation connecting section 110 (which is a single unit with section 105) to section 115.

Figure 2:
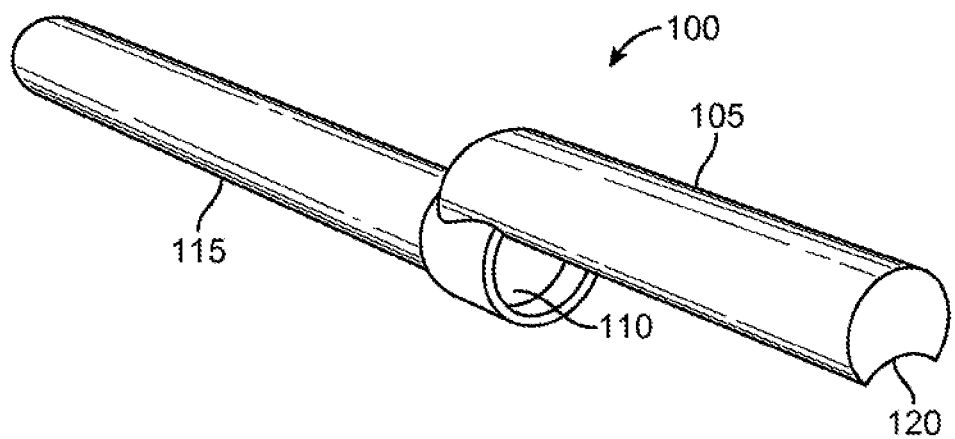
FIG. 2 is an angled view of a spinal rod extension in accordance with an illustrative embodiment.

FIG. 2 is an angled view of a spinal rod extension 100 in accordance with an illustrative embodiment. Section 105 has a curved undersurface 120 that fits onto the top of an existing spinal rod (not shown) and section 110 comprises an opening that accommodates the end of an existing spinal rod (not shown), thus enabling mating of the spinal rod extension to an existing spinal rod (not shown). Section 110 can partially or fully surround the existing spinal rod, depending on the implementation. Section 115 is the extended length of rod that will attach to new pedicle screws (not shown).

Figure 3:
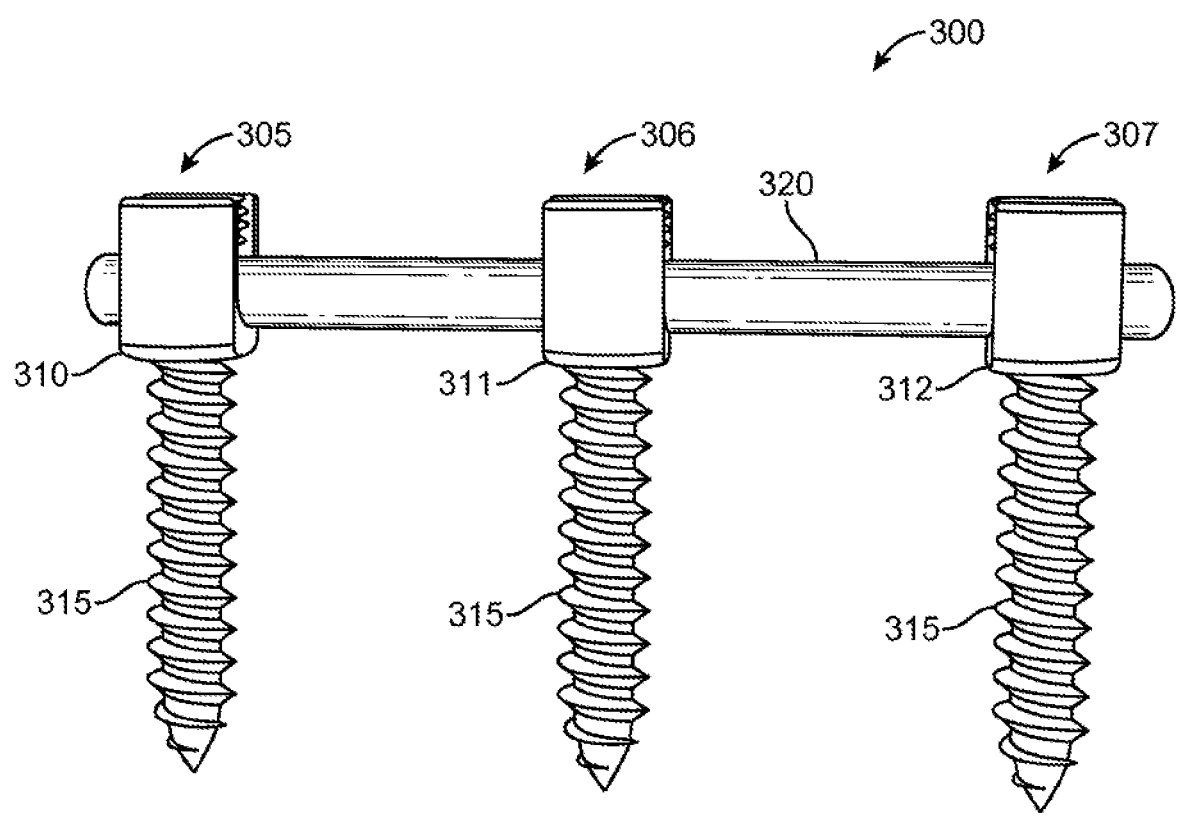
FIG. 3 is a side view of an existing spinal rod attached to three pedicle screws in accordance with an illustrative embodiment.

FIG. 3 is a side view of an existing two-level pedicle screw instrumentation construct 300, in accordance with an illustrative embodiment. The pedicle screw instrumentation construct depicted here would span two intervertebral disk levels while performing a two-level instrumented spinal fusion and includes an existing spinal rod 320 attached to three pedicle screws 305, 306, and 307. The pedicle screws 305, 306, and 307 are comprised of a threaded shaft 315 that in practice would be screwed into a vertebra of a patient (not shown) and a head 310, 311, and 312 that accommodates the existing spinal rod 320.

Figure 4:
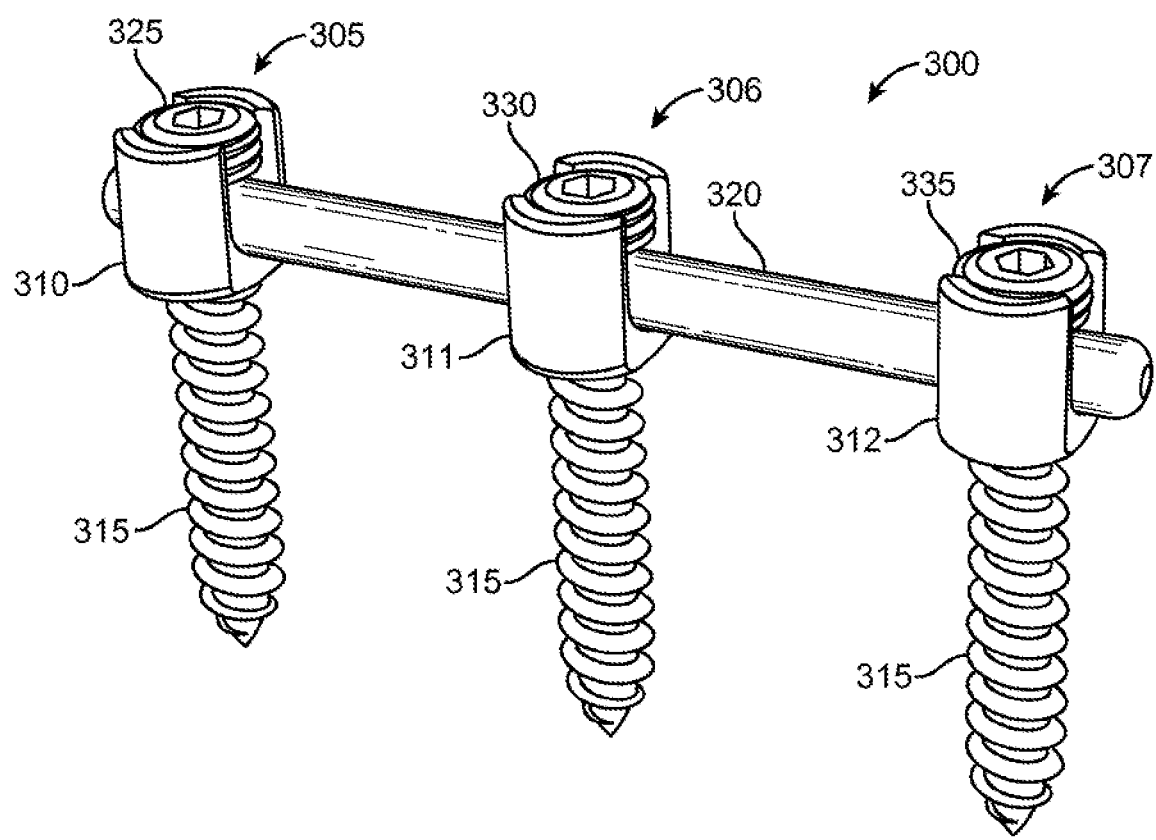
FIG. 4 is an angled view of an existing spinal rod attached to three pedicle screws in accordance with an illustrative embodiment.

FIG. 4 is an angled view of an existing two-level pedicle screw instrumentation construct 300, in accordance with an illustrative embodiment. The pedicle screw instrumentation construct depicted here would span two intervertebral disk levels while performing a two-level instrumented spinal fusion and includes an existing spinal rod 320 attached to three pedicle screws 305, 306, and 307. The pedicle screws are comprised of a threaded shaft 315 that would be screwed into a vertebra of a patient (not shown) and a u-shaped head 310, 311, and 312 that is configured to receive the existing spinal rod 320. Depending on the implementation, a u-shaped head 310, 311, and 312 may be pivotally mounted to the threaded shaft 315 of the pedicle screw. At least an upper portion of the u-shaped head 310, 311, and 312 is threaded and configured to receive a locking cap 325, 330, and 335. The locking cap may be alternatively referred to as a set screw. The existing spinal rod 320 is secured to the pedicle screws by locking caps (or alternatively called set screws) 325, 330, and 335. The locking caps 325, 330, and 335 are used to secure the existing spinal rod 320 such that it remains within the u-shaped head 310, 311, and 312 of the pedicle screw 305, 306, and 307.

Figure 5:
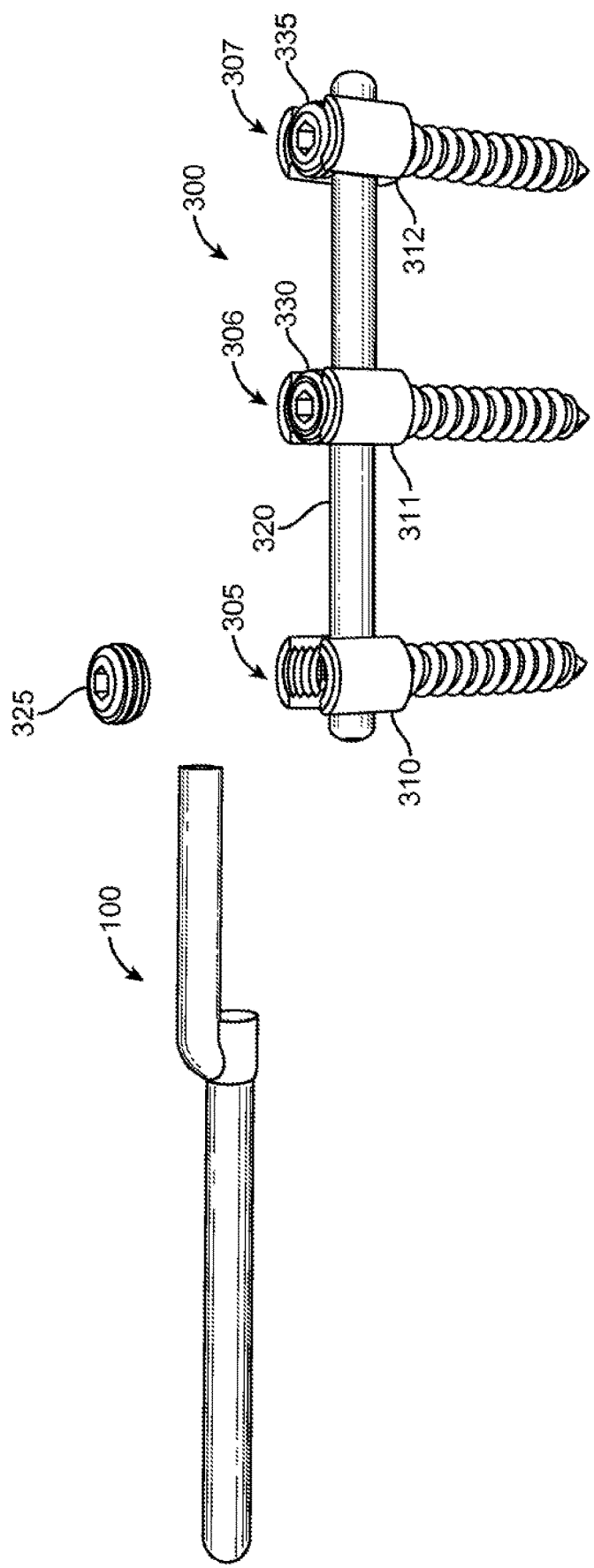
FIG. 5 is an angled view of a spinal rod extension and an existing spinal rod attached to two pedicle screws, with the locking cap of the third pedicle screw removed in anticipation of the spinal rod extension being mounted to the existing spinal rod, in accordance with an illustrative embodiment.

FIG. 5 is an angled view of a spinal rod extension 100 and an existing two-level pedicle screw instrumentation construct 300, in accordance with an illustrative embodiment. Locking cap 325 has been removed from pedicle screw head 310 of pedicle screw 305 in order to create space for the spinal rod extension 100 to mate to existing spinal rod 320. Pedicle screws 306 and 307 have the locking caps 330 and 335 still engaged to pedicle screw heads 311 and 312, thus continuing to attach to rod 320.

Figure 6:
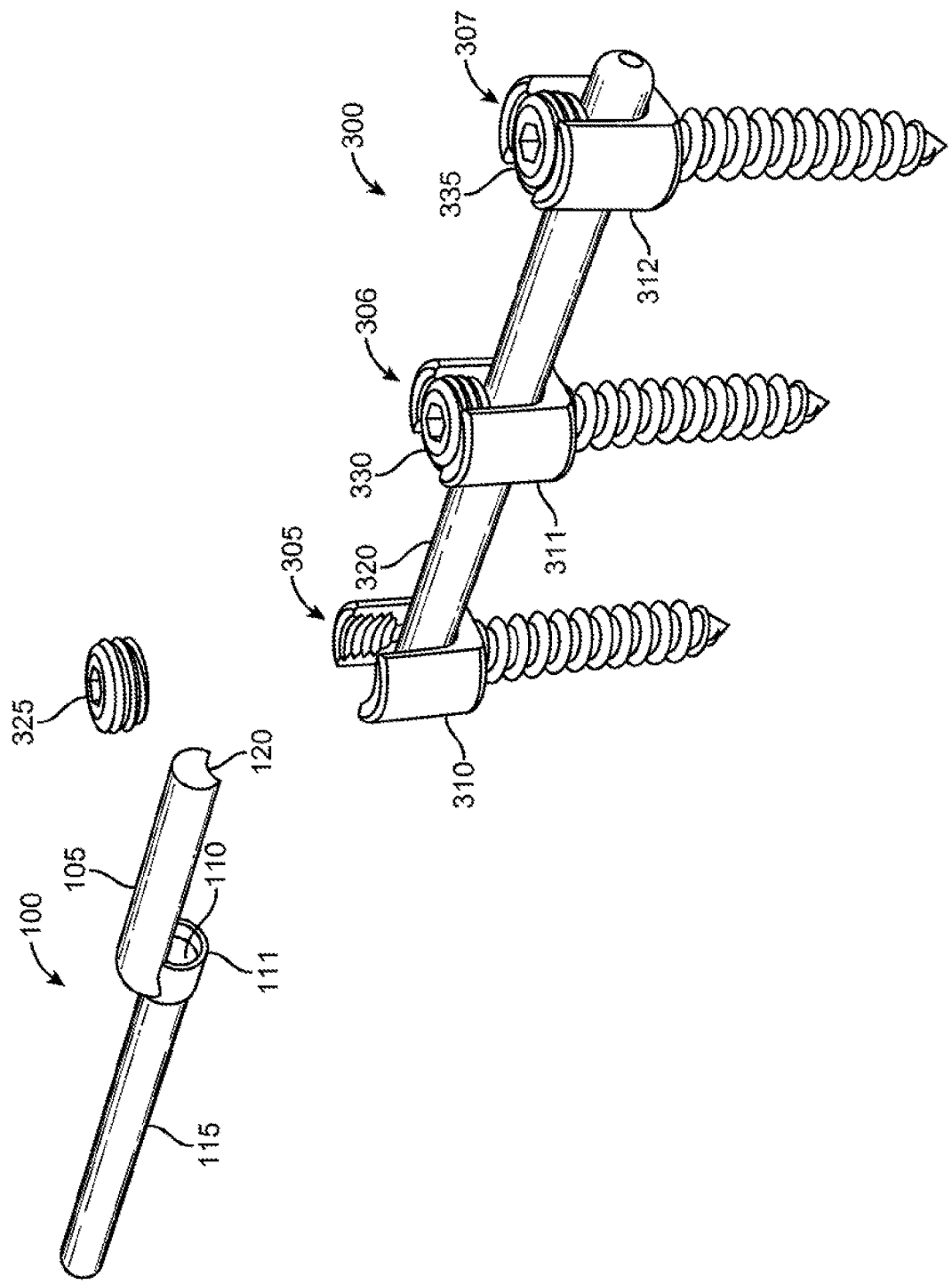
FIG. 6 is an angled view of a spinal rod extension, and an existing spinal rod attached to two pedicle screws, with the locking cap of the third pedicle screw removed in anticipation of the spinal rod extension being mounted to the existing spinal rod, in accordance with an illustrative embodiment.

FIG. 6 is an angled view of a spinal rod extension 100 and an existing two-level pedicle screw instrumentation construct 300, in accordance with an illustrative embodiment. Locking cap 325 has been removed from pedicle screw head 310 of pedicle screw 305 in order to create space for the spinal rod extension 100 to mate to existing spinal rod 320. Pedicle screws 306 and 307 have the locking caps 330 and 335 still engaged to pedicle screw heads 311 and 312, thus continuing to attach to rod 320.

The spinal rod extension 100 can be used to extend the existing spinal rod 320 in the event that the patient with the existing spinal rod 320 needs additional surgery to correct and/or fuse one or more adjacent vertebrae. The spinal rod extension 100 includes a connector portion comprised of an opening 110 which is configured to mate with at least a portion of the terminal end of the existing spinal rod 320 and a section 105 that rests on top of the existing spinal rod and fits intimately by virtue of a concave undersurface 120 that mates with the convex surface of existing spinal rod 320. The spinal rod extension 100 also includes a rod portion 115 that can be used to lengthen the existing spinal rod 320. In an illustrative embodiment, the rod portion 115 and the connector portions 105 and 110 can be molded together or manufactured as a single piece with the rod portion 115 and the connector portions 105 and 110 having various lengths.

In an alternative embodiment, the rod portion 115 may be detachably mounted to the connector portion 110. In such an embodiment, prior to or during surgery, the surgeon can select a rod portion 115 of appropriate length and mount it to the connector portion 110. The mounting can be performed via one or more of a fastener, clamp(s), male/female connection, etc. In another embodiment, the rod portion 115 may articulate relative to the connector portion 110.

In use, the set screw 325 is removed such that the connector portion 105 of the spinal rod extension 100 can be inserted through the u-shaped head 310 of the pedicle screw 305 that was used in the original surgery to secure the existing spinal rod 320. In an illustrative embodiment, a bottom portion (in accordance with the orientation depicted in FIG. 2) of the connector portion 105 can be curved or concave such that the connector portion 105 form-fits the convex contour of the existing spinal rod 320. As such, when mounted to the existing spinal rod 320, the connector portion 105 can be flush with or within a top edge of the u-shaped head 310. In an alternative embodiment, the connector portion 105 may extend slightly beyond the top edge of the u-shaped head 310.

In at least some embodiments, the spinal rod extension 100 includes an opening 110 with a lip 111 that is configured to mate with at least a portion of the terminal end of the existing spinal rod 320 and help secure the spinal rod extension 100 to the existing spinal rod 320. In one embodiment, the lip 111 can be configured to engage just a bottom portion of the existing spinal rod 320 that extends past the u-shaped head 310 of the pedicle screw 305. Alternatively, the lip 111 can form a circular (i.e., rod-shaped) opening 110 that is configured to receive the entire end of the existing spinal rod 320 that extends past the u-shaped head 310 of the pedicle screw 305 and form a male/female connection between the existing spinal rod 320 and the spinal rod extension 100.

Figure 7:
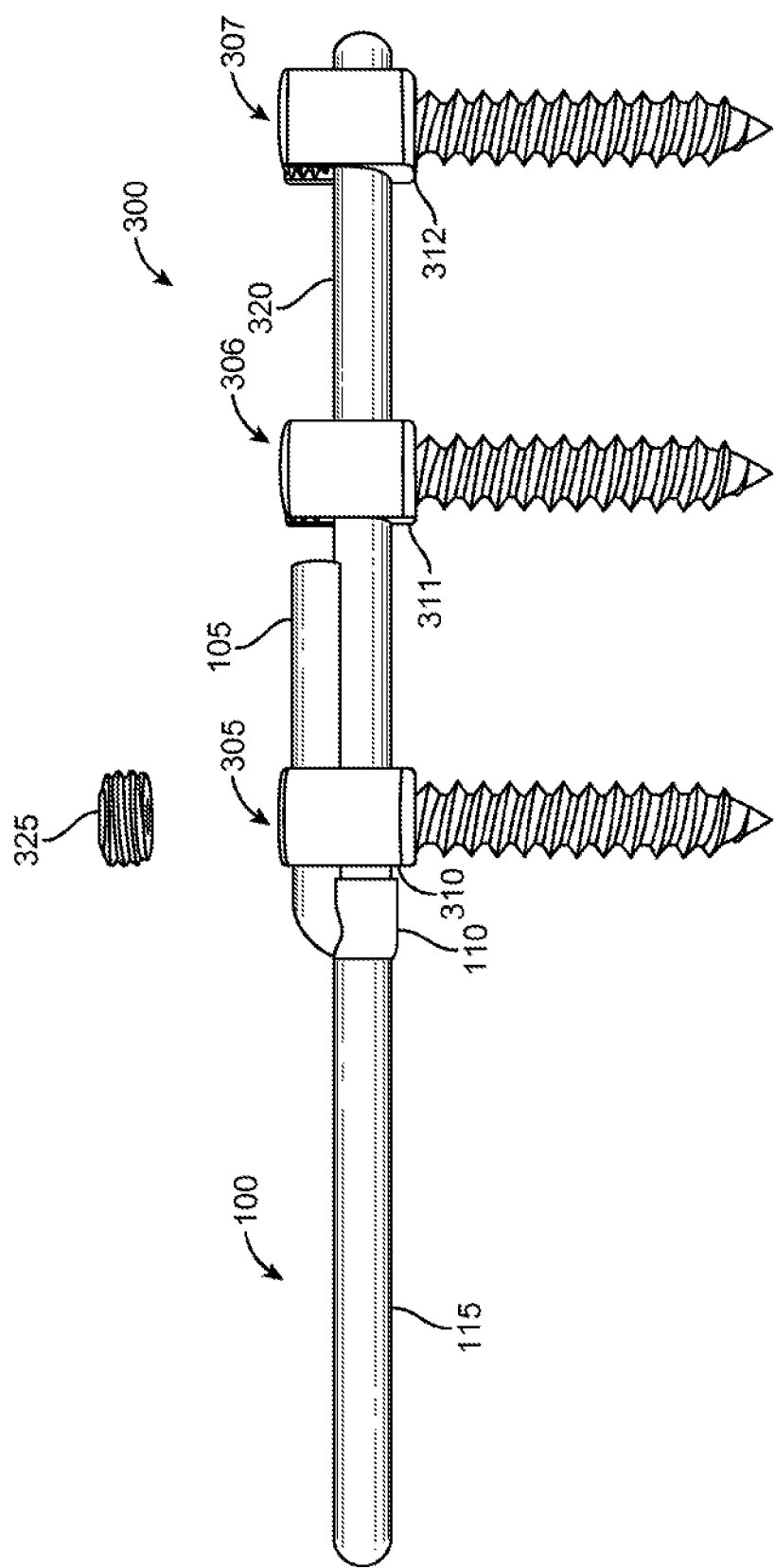
FIG. 7 is a side view of a spinal rod extension, and an existing spinal rod attached to two pedicle screws, with the locking cap of the third pedicle screw removed and the spinal rod extension mounted on the existing spinal rod, in accordance with an illustrative embodiment.

FIG. 7 is a side view of a spinal rod extension 100 mated to an existing spinal rod 320 of an existing two-level pedicle screw instrumentation construct 300, in accordance with an illustrative embodiment. Locking cap 325 has been removed from pedicle screw head 310 of pedicle screw 305, and section 105 of spinal rod extension 100 passes through screw head 310 in the region previously occupied by locking cap 325 and is seated on existing spinal rod 320. Section 110 of spinal rod extension 100 fits around the end of existing spinal rod 320 in a male-female connection configuration, and the extension section 115 of spinal rod extension 100 is available to be secured to new pedicle screws (not shown). Pedicle screws 306 and 307 have the locking caps still engaged to pedicle screw heads 311 and 312, thus continuing to attach to the existing spinal rod 320.

Figure 8:
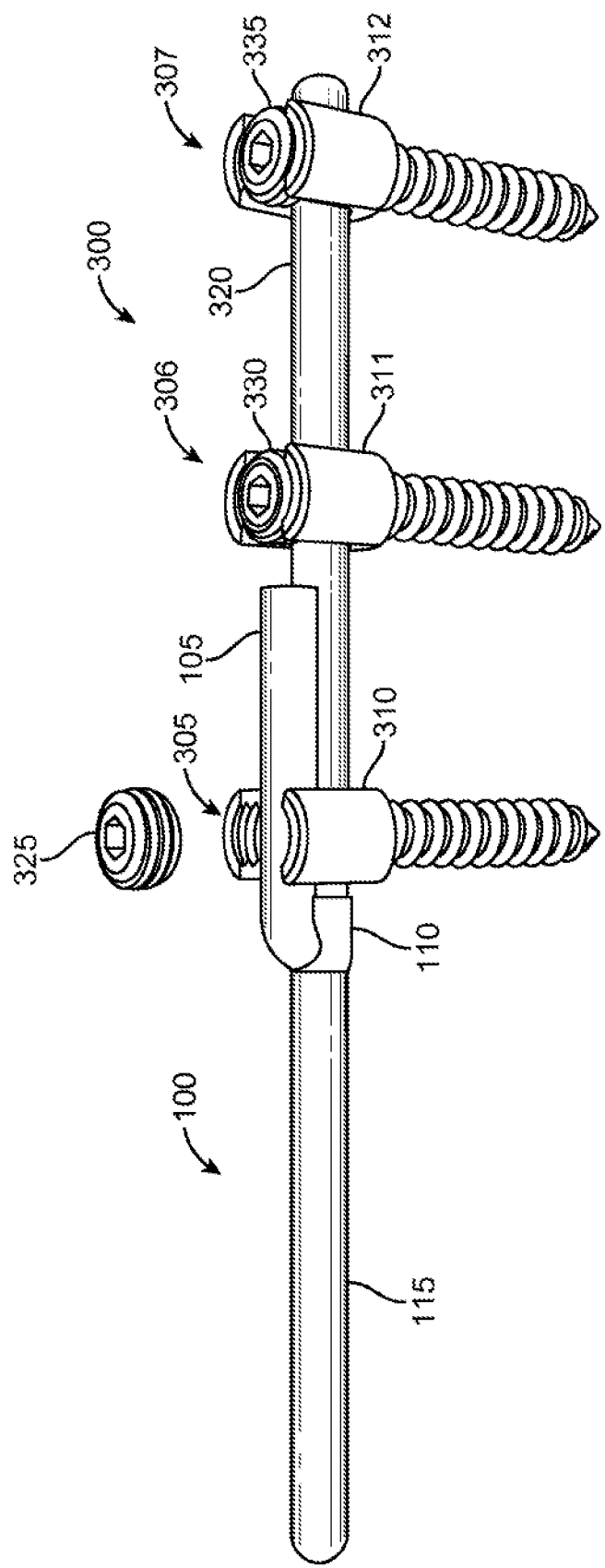
FIG. 8 is an angled view of a spinal rod extension, and an existing spinal rod attached to two pedicle screws, with the locking cap of the third pedicle screw removed and the spinal rod extension mounted on the existing spinal rod, in accordance with an illustrative embodiment.

FIG. 8 is an angled view of a spinal rod extension 100 mated to an existing spinal rod 320 of an existing two-level pedicle screw instrumentation construct 300, in accordance with an illustrative embodiment. Locking cap 325 has been removed from pedicle screw head 310 of pedicle screw 305, and section 105 of spinal rod extension 100 passes through screw head 310 in the region previously occupied by locking cap 325 and is seated on existing spinal rod 320. Section 110 of spinal rod extension 100 fits around the end of existing spinal rod 320, and the extension section 115 of spinal rod extension 100 is available to be secured to new pedicle screws (not shown). Pedicle screws 306 and 307 have the locking caps 330 and 335 still engaged to pedicle screw heads 311 and 312, thus continuing to attach pedicle screws 306 and 307 to the existing spinal rod 320.

Figure 9:
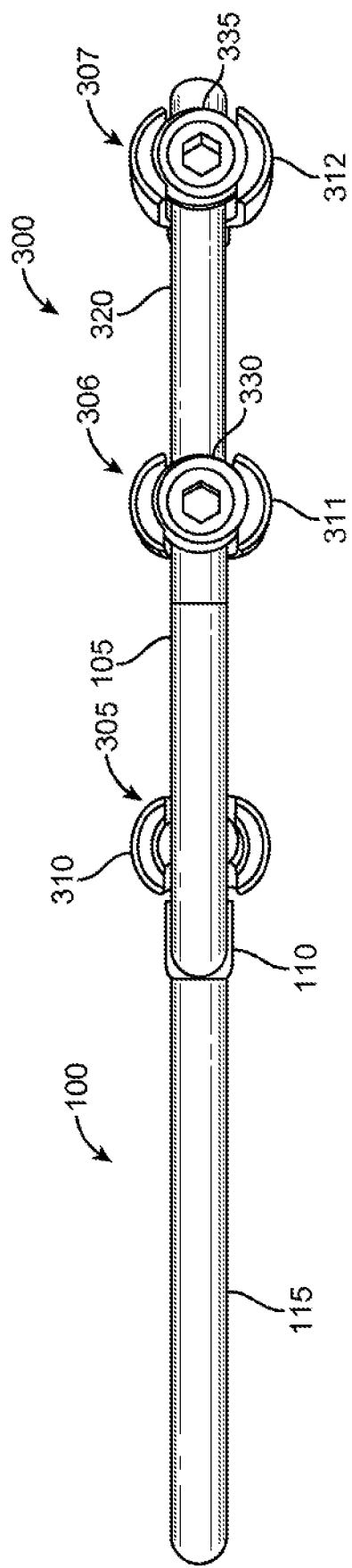
FIG. 9 is a top view of a spinal rod extension, and an existing spinal rod attached to two pedicle screws, with the locking cap of the third pedicle screw removed and the spinal rod extension mounted on the existing spinal rod, in accordance with an illustrative embodiment.

FIG. 9 is a top view of a spinal rod extension 100 mated to an existing spinal rod 320 of an existing two-level pedicle screw instrumentation construct 300, in accordance with an illustrative embodiment. Locking cap 325 (shown in FIG. 8 but no longer shown in FIG. 9) has been removed from pedicle screw head 310 of pedicle screw 305, and section 105 of spinal rod extension 100 passes through screw head 310 in the region previously occupied by locking cap 325 and is seated on existing spinal rod 320. Section 110 of spinal rod extension 100 fits around the end of existing spinal rod 320, and the extension section 115 of spinal rod extension 100 is available to be secured to new pedicle screws (not shown). Pedicle screws 306 and 307 have the locking caps 330 and 335 still engaged to pedicle screw heads 311 and 312, thus continuing to attach pedicle screws 306 and 307 to the existing spinal rod 320.

Figure 10:
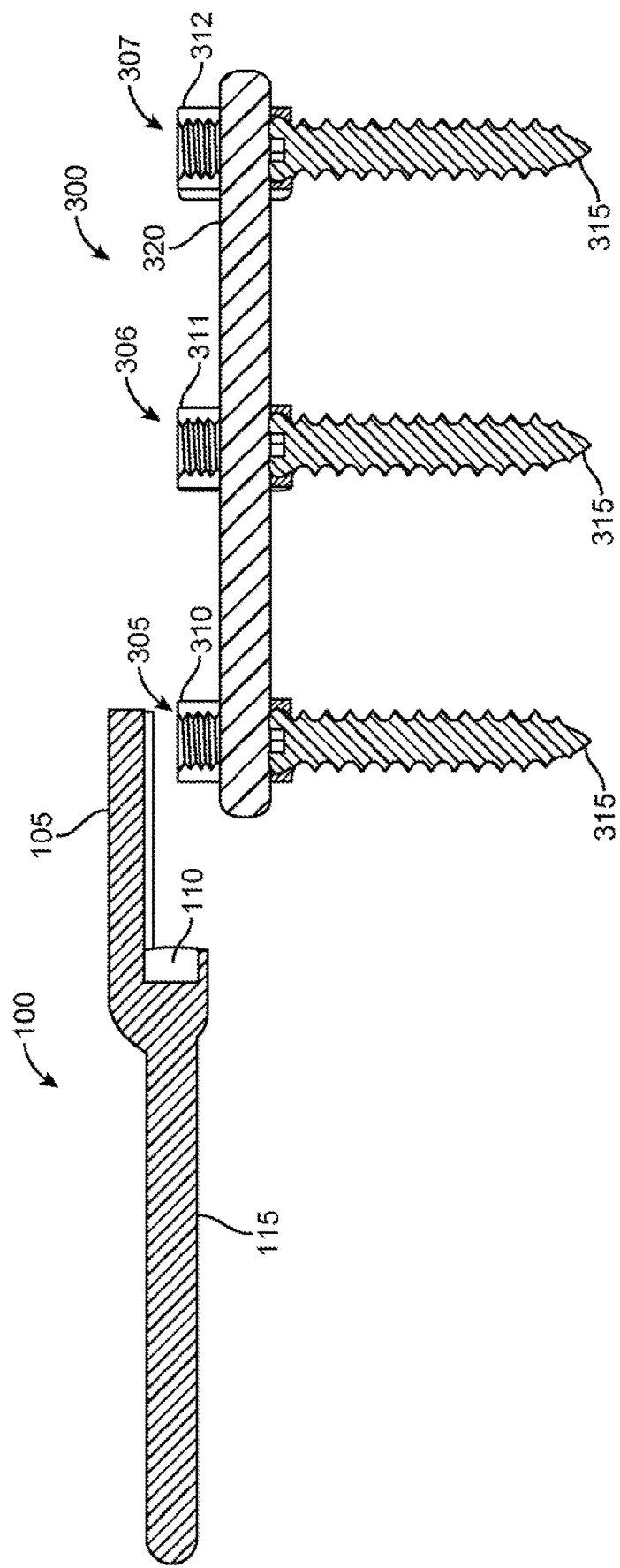
FIG. 10 is a cross sectional view of a spinal rod extension, and an existing spinal rod along with three pedicle screws, in anticipation of the spinal rod extension being mounted on the existing spinal rod, in accordance with an illustrative embodiment.

FIG. 10 is a cross-sectional side view of a spinal rod extension 100 and an existing spinal rod 320 of an existing two-level pedicle screw instrumentation construct 300, in accordance with an illustrative embodiment. Section 110 of spinal rod extension 100 fits around the end of existing spinal rod 320, and the extension section 115 of spinal rod extension 100 is available to be secured to new pedicle screws (not shown). Pedicle screws 306 and 307 would have the locking caps 330 and 335 (shown in FIG. 8, not shown here) still engaged to pedicle screw heads 311 and 312, thus continuing to attach pedicle screws 306 and 307 to the existing spinal rod 320. The threaded shafts 315 of the pedicle screws 305, 306, and 307 are shown. Locking cap 325 (shown in FIG. 8 but no longer shown in FIG. 10) has been removed from pedicle screw head 310 of pedicle screw 305, and section 105 of spinal rod extension 100 passes through screw head 310 in the region previously occupied by locking cap 325 and is seated on existing spinal rod 320.

Figure 11:
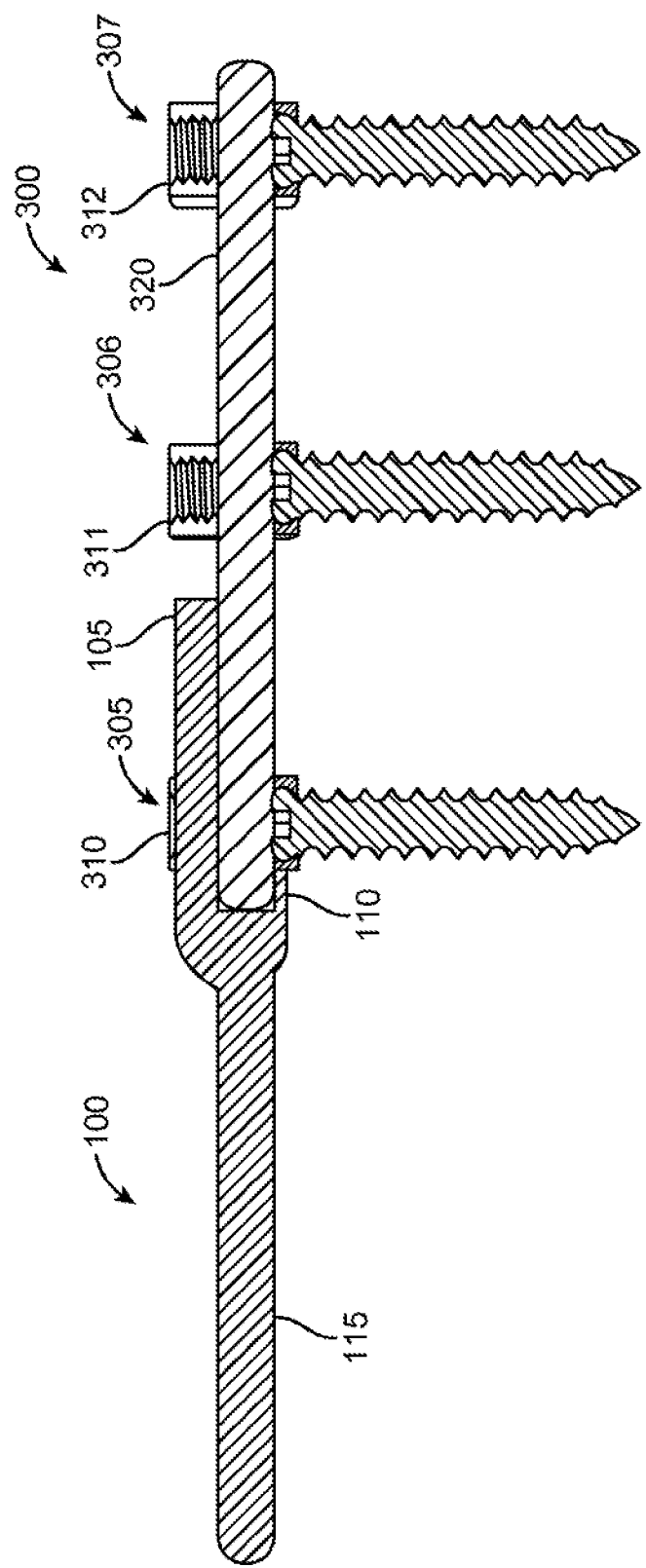
FIG. 11 is a cross sectional view of a spinal rod extension, and an existing spinal rod along with three pedicle screws, with the spinal rod extension mounted on the existing spinal rod, in accordance with an illustrative embodiment.

FIG. 11 is a cross-sectional side view of a spinal rod extension 100 mated to an existing spinal rod 320 of an existing two-level pedicle screw instrumentation construct 300, in accordance with an illustrative embodiment. Section 110 of spinal rod extension 100 fits around the end of existing spinal rod 320, and the extension section 115 of spinal rod extension 100 is available to be secured to new pedicle screws (not shown). Locking cap 325 (shown in FIG. 8 but no longer shown here) has been removed from pedicle screw head 310 of pedicle screw 305, and section 105 of spinal rod extension 100 passes through screw head 310 in the region previously occupied by locking cap 325 and is seated on existing spinal rod 320. Pedicle screws 306 and 307 would have the locking caps 330 and 335 (shown in FIG. 8, not shown here) still engaged to pedicle screw heads 311 and 312, thus continuing to attach pedicle screws 306 and 307 to the existing spinal rod 320.

Figure 12:
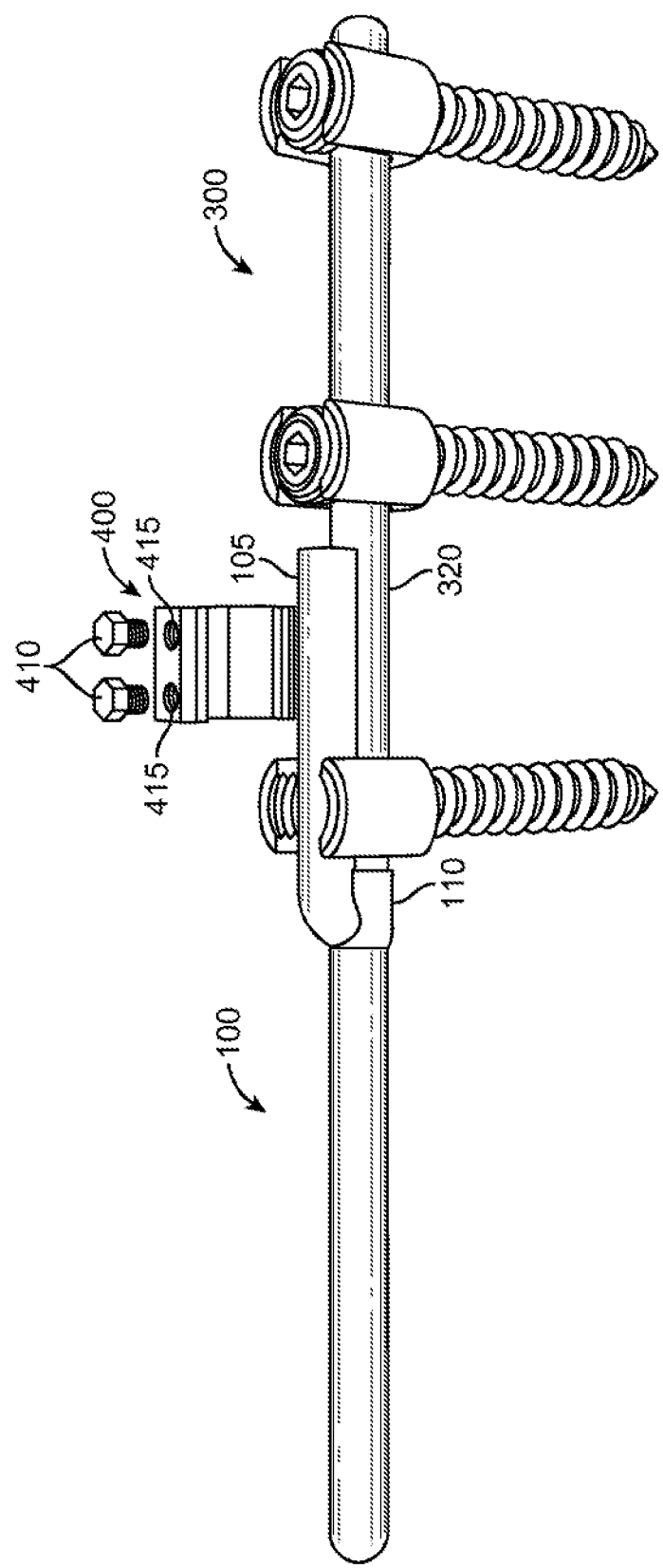
FIG. 12 is an angled view of a spinal rod extension mounted on an existing spinal rod, in anticipation of a clamp being applied to secure the spinal rod extension to the existing spinal rod, in accordance with an illustrative embodiment.

FIG. 12 is an angled view of a spinal rod extension 100 mated to an existing spinal rod 320 of an existing two-level pedicle screw instrumentation construct, as also seen in FIG. 8, in this figure prepared to be secured by a clamp 400, in accordance with an illustrative embodiment. The clamp 400 can be any type of circular clamp known to those of skill in the art. In one embodiment, the clamp 400 can be a C-shaped partial ring with one side open such that the clamp could be slipped around both the connector portion 105 and the existing rod 320 from the side and then secured with one or more bolt(s) or screw(s) 410. In another embodiment, the clamp 400 can be a ring-shape that has a hinge on one side and a latch on the other side so that the clamp 400 is able to slide around the connector portion 105 and the existing rod 320 and then be latched into a closed position, thus securing the connector portion 105 to the existing rod 320. Another embodiment of the clamp 400 would be to use a strong woven fiber tape which could pass around both the connector portion 105 and the existing rod 320, and then be tied together or otherwise secured. Yet another embodiment of the clamp 400 can be a circular hose clamp that can be loosened and tightened via a screwdriver or other tool.

Clamp 400 is prepared to secure the spinal rod section 105 and its other sections comprising spinal rod extension 100 in its entirety to the existing spinal rod 320. Once the clamp is positioned around the spinal rod extension and existing spinal rod, it will be tightened via bolts or set screws 410 which screw into threaded holes 415 and press against rod extension section 105, thus securing spinal rod extension 100 to the existing spinal rod 320. The bolts or set screws 410 can be tightened such that ends of the bolts or set screws contact the top surface of the spinal rod extension section 105, thereby causing a friction fit between the connector portion 105 and the existing spinal rod 320. The friction fit is maintained by the opening 110 and/or lip 111 (111 not shown) and the relationship of the concave undersurface of rod extension connector portion 105 to the convex surface of existing rod 320 and the clamp 400. In an alternative embodiment, the set screws 410 can be placed through threaded holes created in the rod extension section 105 itself, and create a frictional fit with existing rod 320.

One or more clamps may be used. In an alternative embodiment, more than one clamp may be used. In another alternative embodiment, the clamp may be smaller or larger and may use one bolt or may use three or more bolts to secure the clamp(s) to the rods. In another alternative embodiment, clamp 400 may be of any style or configuration that results in spinal rod extension 100 being secured to existing spinal rod 320.

Figure 13:
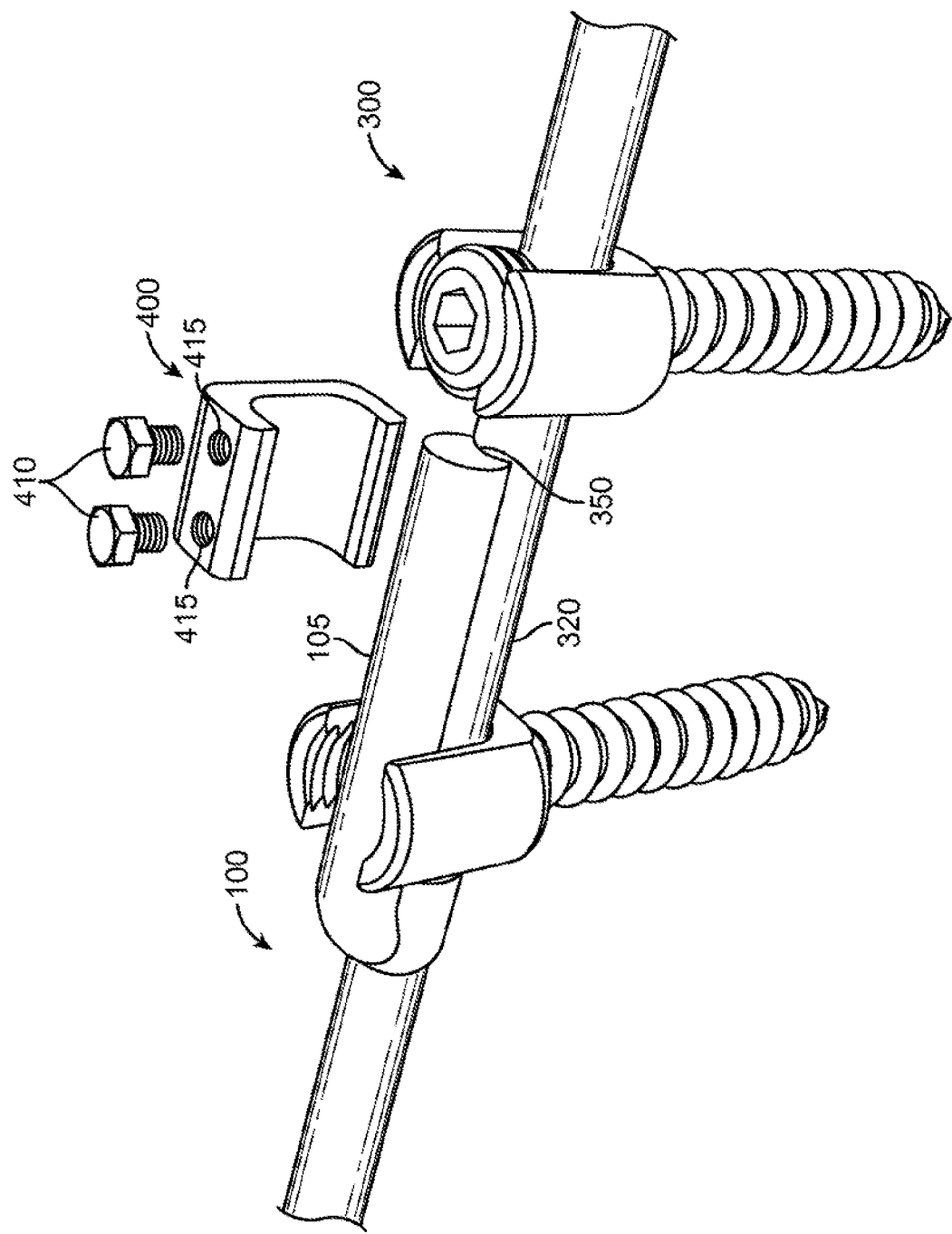
FIG. 13 is an angled close-up view of the area of connection of a spinal rod extension mounted to an existing spinal rod, in anticipation of a clamp being applied to secure the spinal rod extension to the existing spinal rod, in accordance with an illustrative embodiment.

FIG. 13 is an angled close-up view of a portion of spinal rod extension 100 mated to an existing spinal rod 320 of an existing two-level pedicle screw instrumentation construct, as also seen in FIG. 8 and FIG. 12, in accordance with an illustrative embodiment. Clamp 400 is prepared to secure the spinal extension rod section 105 and its other sections comprising spinal rod extension 100 in its entirety to the existing spinal rod 320. Once the clamp is positioned around the spinal rod extension and existing spinal rod, it will be tightened via bolts 410 which screw into threaded holes 415 and press against rod extension section 105, thus securing spinal rod extension 100 to the existing spinal rod 320. The curved concave undersurface of spinal rod extension section 105 is shown 350 to mate to the concave surface of existing spinal rod 320.

Figure 14:
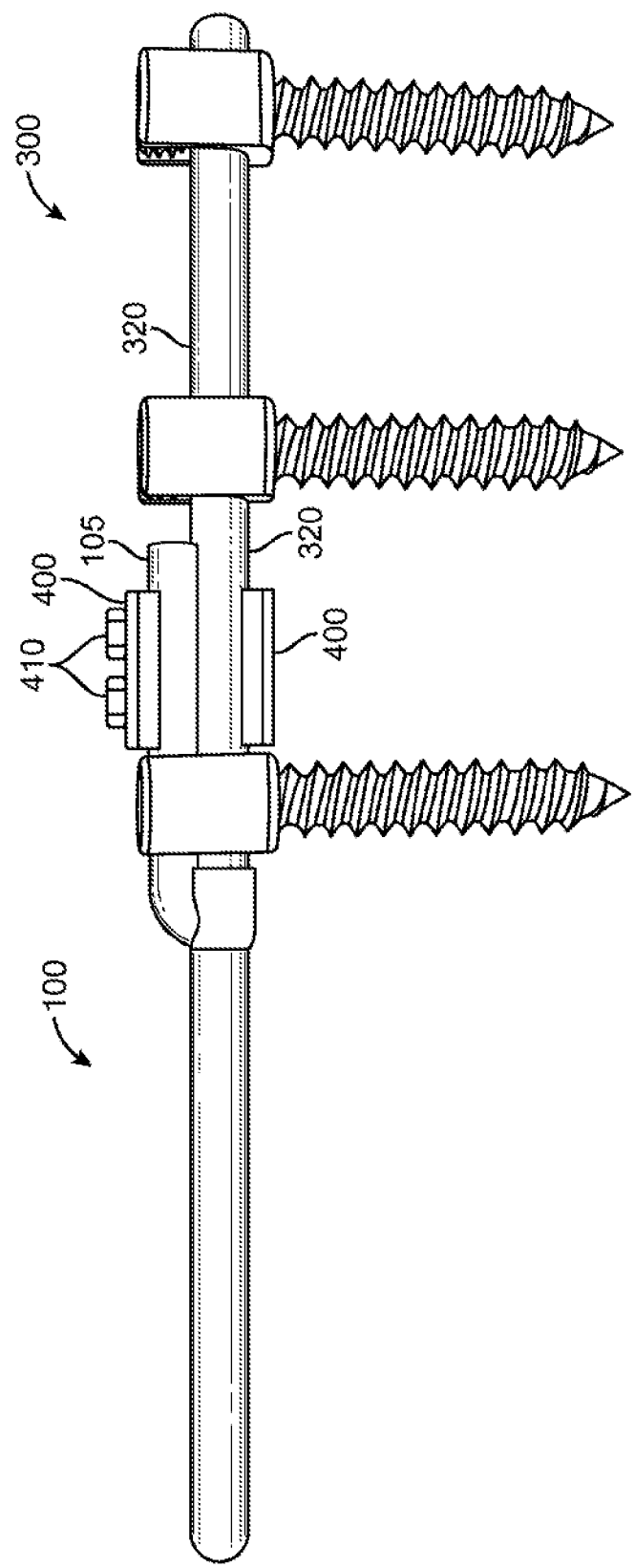
FIG. 14 is a side view of a spinal rod extension mounted on an existing spinal rod, with a clamp securing the spinal rod extension to the existing spinal rod, in accordance with an illustrative embodiment.

FIG. 14 is a side view of a spinal rod extension 100 mated to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320.

Figure 15:
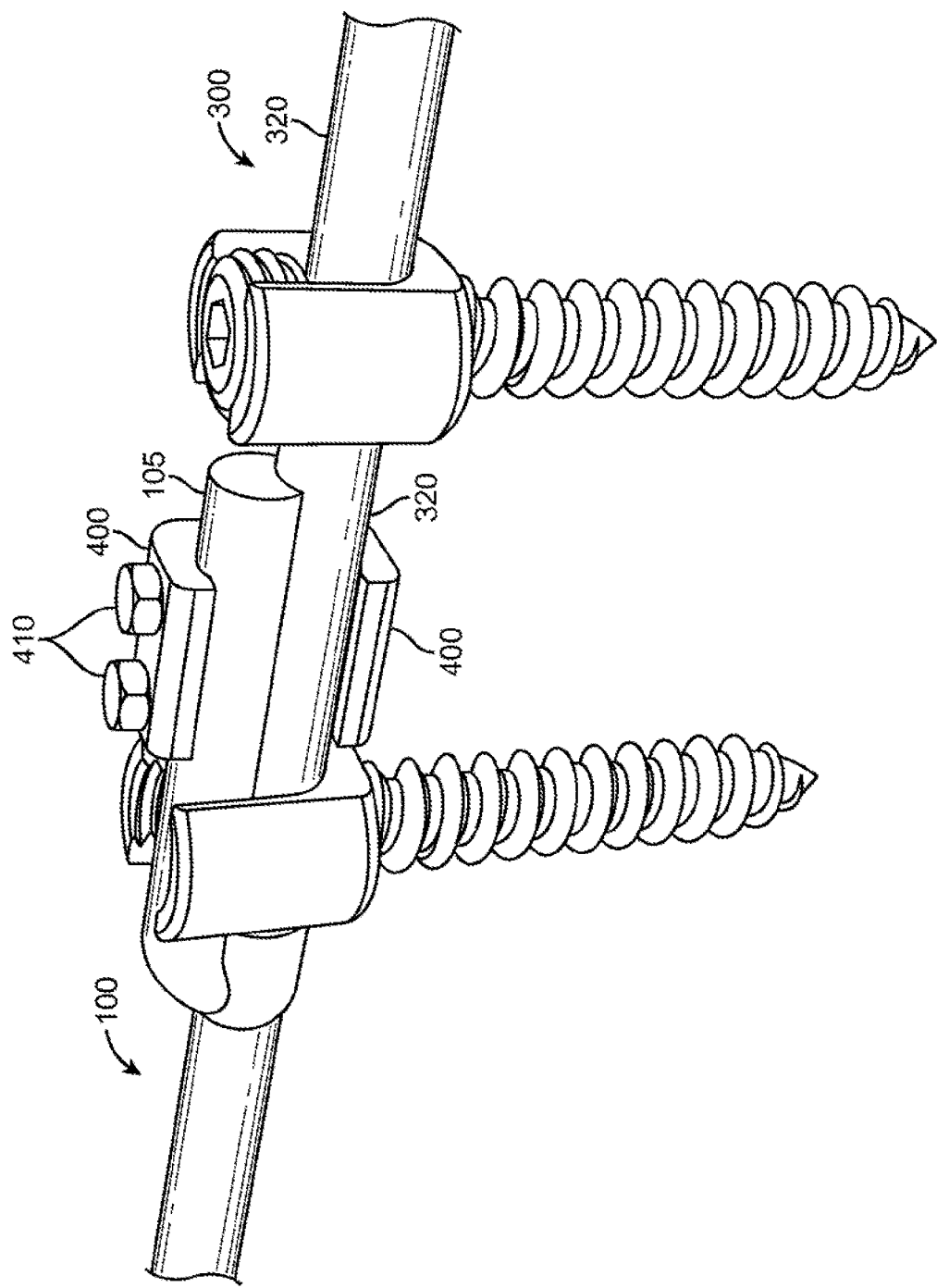
FIG. 15 is an angled close-up view of a spinal rod extension mounted on an existing spinal rod, with a clamp securing the spinal rod extension to the existing spinal rod, in accordance with an illustrative embodiment.

FIG. 15 is an angled close-up view of a spinal rod extension 100 mated to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320.

Figure 16:
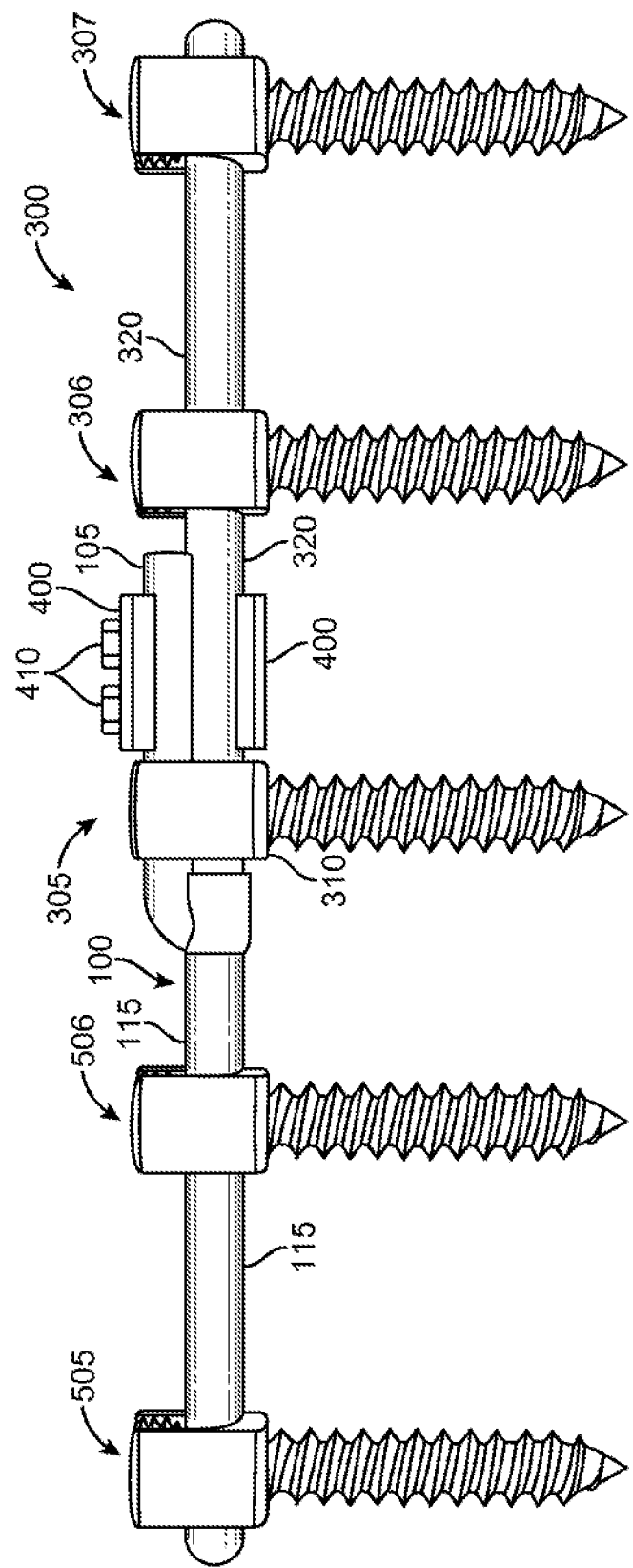
FIG. 16 is a side view of a spinal rod extension mounted on an existing spinal rod, with a clamp securing the spinal rod extension to the existing spinal rod, in accordance with an illustrative embodiment. The existing spinal rod is secured to two pedicle screws with locking caps, the spinal rod extension is now secured to two pedicle screws with locking caps, and both the spinal rod extension and the existing spinal rod are seated in the central pedicle screw head but are not attached to this pedicle screw with a locking cap.

FIG. 16 is a side view of a spinal rod extension 100 attached to new pedicle screws 505 and 506 and secured via clamp 400 to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320. Existing pedicle screws 306 and 307 are secured via locking caps to existing spinal rod 320, the locking cap has been removed from pedicle screw 305 so that section 105 can pass through the pedicle screw head 310, and new pedicle screws 505 and 506 are secured via locking caps to spinal rod extension section 115, thus allowing for extension of an existing spinal instrumentation construct to a new level or levels. In this embodiment, existing spinal instrumentation is a two-level construct and the rod extension attaches to two new levels. In practice, the existing spinal instrumentation may be two or more levels and the extension can be attached to one or more new levels as clinically indicated. The spinal rod extension can be made in different lengths to accommodate different length constructs.

Figure 17:
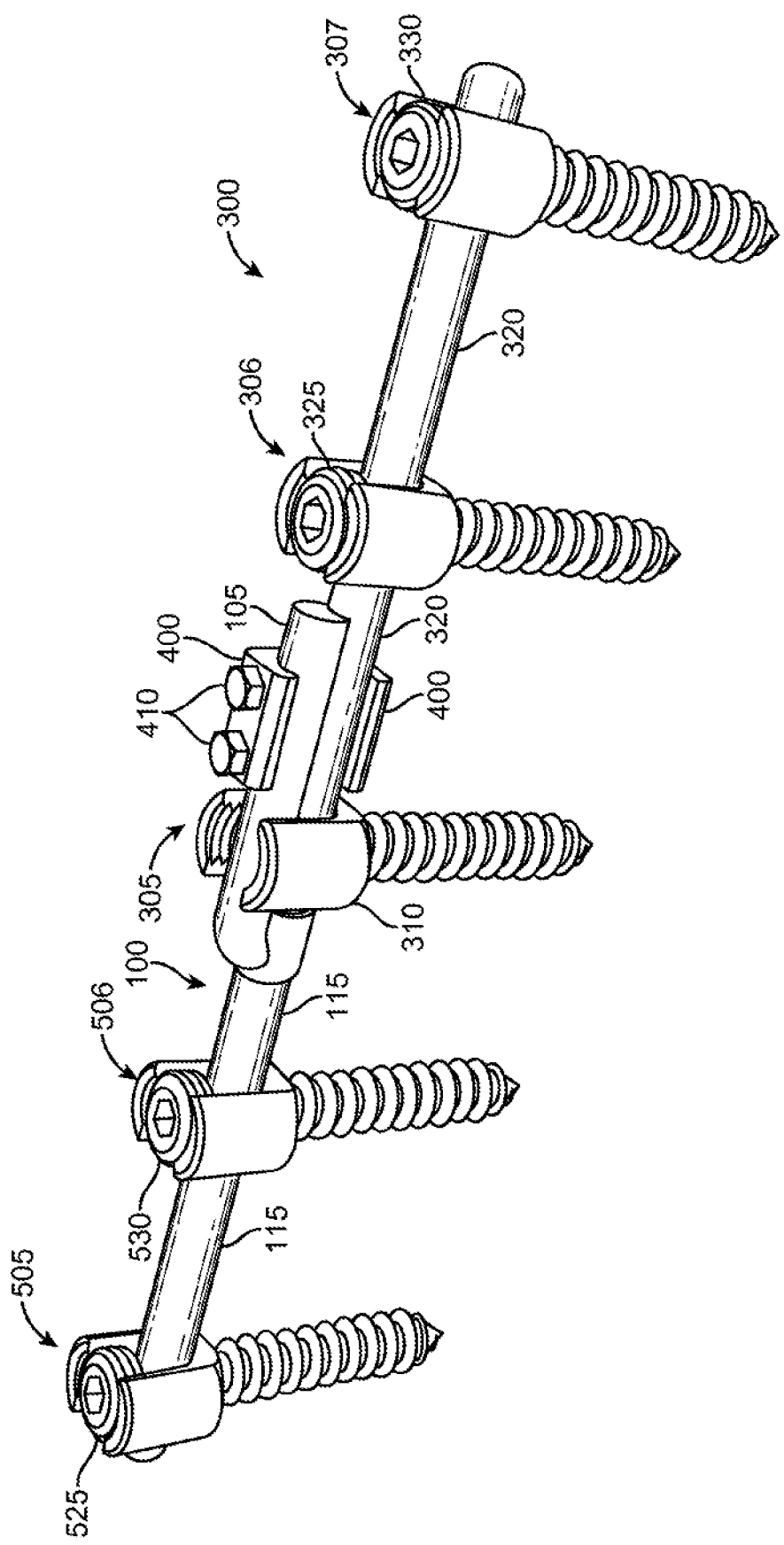
FIG. 17 is an angled view of a spinal rod extension mounted on an existing spinal rod, with a clamp securing the spinal rod extension to the existing spinal rod, in accordance with an illustrative embodiment. The existing spinal rod is secured to two pedicle screws with locking caps, the spinal rod extension is now secured to two pedicle screws with locking caps, and both the spinal rod extension and the existing spinal rod are seated in the central pedicle screw head but are not attached to this pedicle screw with a locking cap.

FIG. 17 is an angled view of a spinal rod extension 100 attached to new pedicle screws 505 and 506 and secured via clamp 400 to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320. Existing pedicle screws 306 and 307 are secured via locking caps 325 and 330 to existing spinal rod 320, and new pedicle screws 505 and 506 are secured via locking caps 525 and 530 to spinal rod extension section 115, thus allowing for extension of an existing spinal instrumentation construct to a new level or levels. The spinal rod extension passes through pedicle screw head 310 of pedicle screw 305, with the locking cap that originally was present in screw head 310 having been permanently removed. In an alternative embodiment, locking cap 325 could be removed from pedicle screw head 311 of pedicle screw 306 and a longer section 105 of spinal rod extension 100 could pass through both screw heads 310 and 311 and the spinal rod extension secured to the existing spinal rod in one or more places with one or more clamps. In the embodiment shown in FIG. 17, the existing spinal instrumentation is a two-level construct spanning two intervertebral disk spaces and the spinal rod extension attaches to two new levels. In practice, the existing spinal instrumentation may be two or more levels and the spinal rod extension can be attached to one or more new levels as clinically indicated. The spinal rod extension can be made in different lengths to accommodate different length constructs.

Figure 18:
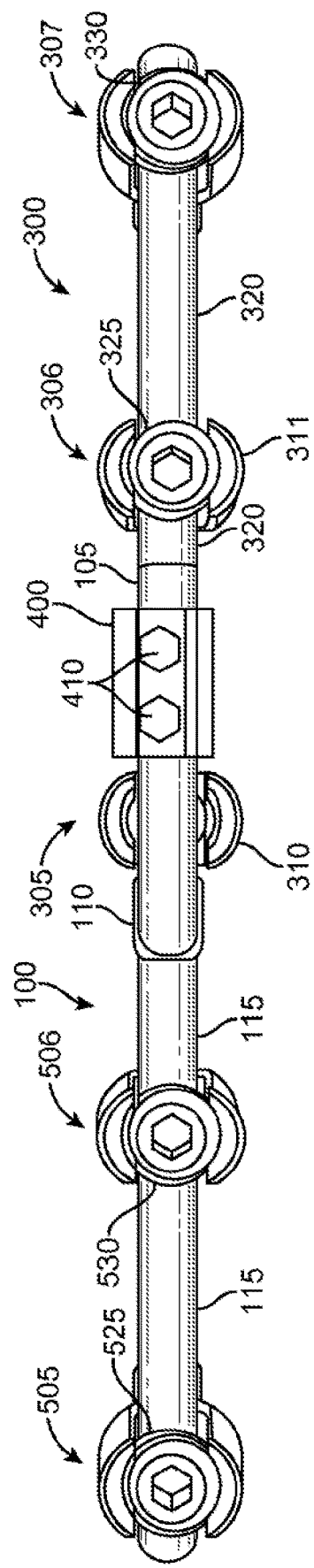
FIG. 18 is a top view of a spinal rod extension mounted on an existing spinal rod, with a clamp securing the spinal rod extension to the existing spinal rod, in accordance with an illustrative embodiment. The existing spinal rod is secured to two pedicle screws with locking caps, the spinal rod extension is now secured to two pedicle screws with locking caps, and both the spinal rod extension and the existing spinal rod are seated in the central pedicle screw head but are not attached to this pedicle screw with a locking cap.

FIG. 18 is a top view of a spinal rod extension 100 attached to new pedicle screws 505 and 506 and secured via clamp 400 to an existing spinal rod 320 of an existing two-level pedicle screw instrumentation construct 300, in accordance with an illustrative embodiment. Clamp 400 is securing the spinal rod section 105 and its other sections comprising spinal rod extension 100 in its entirety to the existing spinal rod 320. The clamp is positioned around the spinal rod extension and existing spinal rod, and is tightened via bolts 410 which have been screwed into threaded holes 415 (shown in FIG. 12, not shown here) and press against rod extension section 105, thus securing spinal rod extension 100 to the existing spinal rod 320. Existing pedicle screws 306 and 307 are secured via locking caps 325 and 330 to existing spinal rod 320, and new pedicle screws 505 and 506 are secured via locking caps 525 and 530 to spinal rod extension section 115, thus allowing for extension of an existing spinal instrumentation construct to a new level or levels. The spinal rod extension passes through pedicle screw head 310 of pedicle screw 305, with the locking cap that originally was present in screw head 310 having been permanently removed. In an alternative embodiment, locking cap 325 could be removed from pedicle screw head 311 of pedicle screw 306 and a longer section 105 of spinal rod extension 100 could pass through both screw heads 310 and 311 and the spinal rod extension secured to the existing spinal rod in one or more places with one or more clamps. In an alternative embodiment, section 105 of spinal rod extension 100 can pass through more than two existing pedicle screw heads. In the embodiment shown in FIG. 18, the existing spinal instrumentation is a two-level construct spanning two intervertebral disk spaces and the spinal rod extension attaches to two new vertebral levels via pedicle screws. In practice, the existing spinal instrumentation may be two or more levels and the spinal rod extension can be attached to one or more new levels as clinically indicated. The spinal rod extension can be made in different lengths to accommodate different length constructs.

As discussed above with reference to FIG. 18, the spinal rod extension passes through pedicle screw head 310 of pedicle screw 305, with the locking cap that originally was present in screw head 310 having been permanently removed. In an alternative embodiment, the locking cap that was originally present in screw head 310 may be temporarily removed to accommodate the spinal rod extension. Upon placement of the spinal rod extension, the locking cap can be reinserted into the screw head 310 and used to secure or help secure the existing spinal rod.

Figure 19:
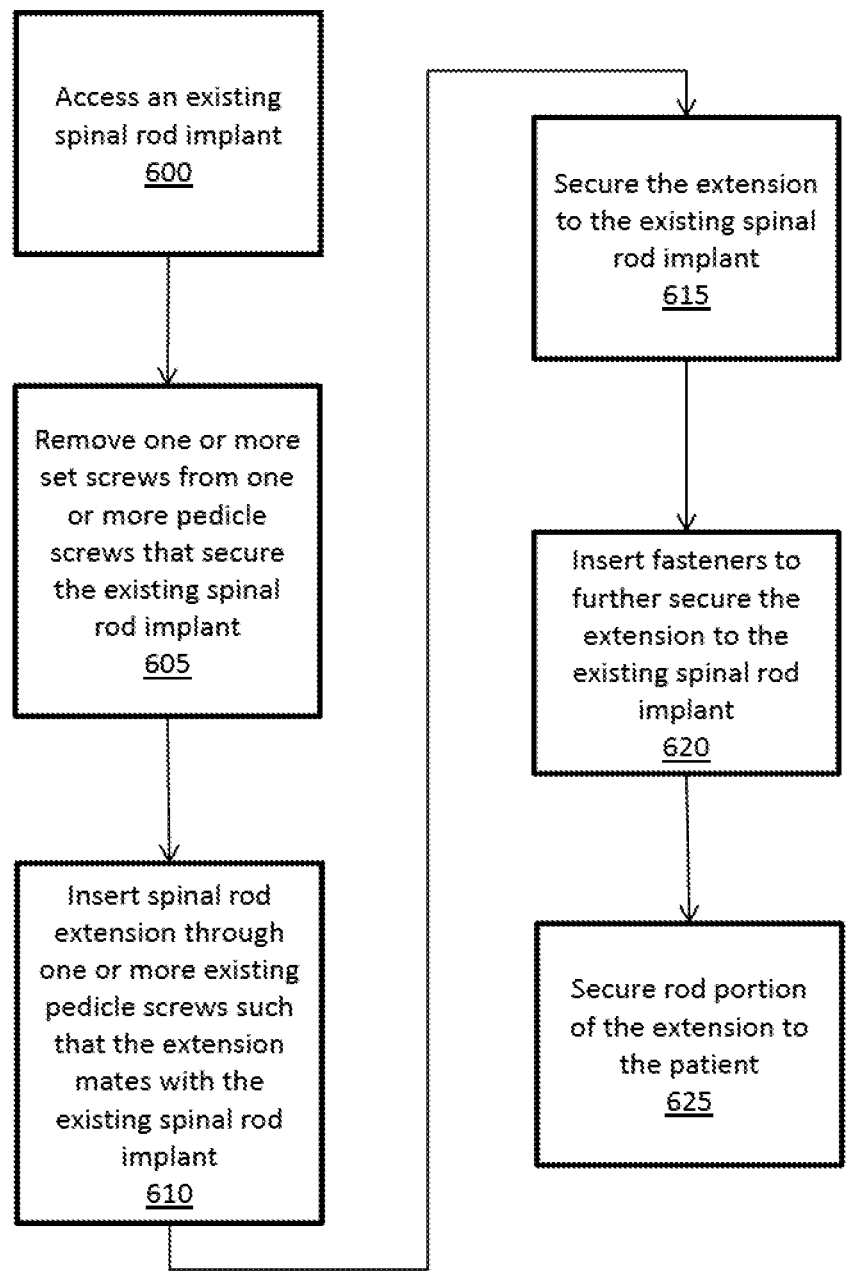
FIG. 19 is a flow diagram depicting a process for mounting a spinal rod extension to an existing spinal rod in accordance with an illustrative embodiment.

FIG. 19 is a flow diagram depicting a process for mounting a spinal rod extension to an existing spinal rod in accordance with an illustrative embodiment. In alternative embodiments, fewer, additional, and/or different operations may be performed. Additionally, the use of a flow diagram is not meant to be limiting with respect to the order of operations performed. In an operation 600, the surgeon accesses an existing spinal rod implant in a patient. Specifically, the surgeon can surgically approach the top or the bottom of the existing spinal rod and terminal pedicle screw, depending on where the spinal rod extension is to be placed.

In an operation 605, the surgeon removes one or more set screws (or locking caps) from one or more pedicle screws that secure the existing spinal rod. Upon removal of the one or more set screws, the existing spinal rod is exposed. In an operation 610, the surgeon inserts the spinal rod extension through the one or more existing pedicle screws from which the one or more set screws were removed. Specifically, the spinal rod extension is placed dorsally onto the existing spinal rod, passing through the pedicle screw u-shaped head(s) from with the set screw(s) have been removed. In an illustrative embodiment, the spinal rod extension is positioned so that a lip or opening of the spinal rod extension engages an end of the existing spinal rod that extends past a terminal pedicle screw that was used to secure the existing spinal rod.

In an operation 615, the spinal rod extension is secured to the existing spinal rod implant. In an illustrative embodiment, the spinal rod extension is secured to the existing spinal rod with one or more clamps. In alternative embodiments, a different securing method may be used. In an operation 620, the surgeon inserts fasteners to further secure the spinal rod extension to the existing spinal rod.

In an operation 625, the surgeon secures the rod portion of the spinal rod extension to the patient. In an illustrative embodiment, the spinal rod extension is attached to new pedicle screws that are placed cephalad or caudal to the existing spinal rod, depending on the needs of the patient. The rod portion of the spinal rod extension can be tunneled beneath the skin, subcutaneous tissues, and muscle of the patient in order to attach to the new pedicle screws that have been placed percutaneously. Alternatively, the rod portion of the spinal rod implant can be attached to new pedicle screws that have been placed through a conventional open posterior approach.

The spinal rod extensions described herein can be made of the same materials as existing spinal instrumentation systems, which include but are not limited to titanium, titanium alloy, cobalt-chrome, stainless steel, and polyether ether ketone (PEEK). The spinal rod extension can be provided as a straight version (i.e., a version in which the rod portion of the spinal rod extension is substantially straight) that can be placed as-is into the patient. The spinal rod extension can also be flexible such that the rod portion of the spinal rod extension can be bent prior to implantation in order to match the patient's anatomy. The spinal rod extension can also be provided as a pre-contoured version in which the rod portion is pre-bent to match a patient's lordotic or kyphotic spine segment.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of mounting a spinal rod extension, the method comprising:
   accessing at least a portion of an existing spinal rod;
   removing a locking cap from an existing pedicle screw that secures the existing spinal rod;
   placing a connector portion of the spinal rod extension through a screw head of the existing pedicle screw; and
   using a connector to secure the connector portion to the existing spinal rod, wherein using the connector comprises placing one or more fasteners through one or more openings in the connector portion.

2. The method of claim 1, further comprising aligning a lip of the connector portion such that the lip engages at least a portion of an end of the existing spinal rod.

3. The method of claim 1, further comprising securing a rod portion of the spinal rod extension to one or more vertebra.

4. The method of claim 1, wherein using the connector further comprises using a clamp to secure the connector portion to the existing spinal rod.

5. The method of claim 1, further comprising re-inserting the locking cap of the existing pedicle screw to help secure the connector portion to the existing spinal rod.

6. The method of claim 1, further comprising aligning a concave surface of the connector portion with the existing spinal rod such that the concave surface mates with the existing spinal rod.

7. The method of claim 1, wherein the connector includes a C-clamp, a hose clamp, or a multi-piece circle clamp.

\* \* \* \* \*